US011987645B2

(12) United States Patent
Song et al.

(10) Patent No.: US 11,987,645 B2
(45) Date of Patent: May 21, 2024

(54) PEPTIDE FOR TREATING RHEUMATOID ARTHRITIS AND USE THEREOF

(71) Applicant: SEOUL NATIONAL UNIVERSITY R&DB FOUNDATION, Seoul (KR)

(72) Inventors: Yeong Wook Song, Seoul (KR); Joo Youn Lee, Gimpo-si (KR); Eugene C. Yi, Seoul (KR); Min Jueng Kang, Seoul (KR)

(73) Assignee: SEOUL NATIONAL UNIVERSITY R&DB FOUNDATION, Seoul (KR)

( * ) Notice: Subject to any disclaimer, the term of this patent is extended or adjusted under 35 U.S.C. 154(b) by 608 days.

(21) Appl. No.: 17/257,492

(22) PCT Filed: Jul. 2, 2019

(86) PCT No.: PCT/KR2019/008040
§ 371 (c)(1),
(2) Date: Dec. 31, 2020

(87) PCT Pub. No.: WO2020/009424
PCT Pub. Date: Jan. 9, 2020

(65) Prior Publication Data
US 2021/0221847 A1 Jul. 22, 2021

(30) Foreign Application Priority Data
Jul. 3, 2018 (KR) .................. 10-2018-0077329
Jul. 1, 2019 (KR) .................. 10-2019-0078953

(51) Int. Cl.
C07K 7/08 (2006.01)
A23L 33/00 (2016.01)
A23L 33/18 (2016.01)
A61K 38/00 (2006.01)
A61P 19/02 (2006.01)
G01N 33/92 (2006.01)

(52) U.S. Cl.
CPC .............. C07K 7/08 (2013.01); A23L 33/18 (2016.08); A23L 33/40 (2016.08); A61P 19/02 (2018.01); G01N 33/92 (2013.01); A23V 2002/00 (2013.01); A61K 38/00 (2013.01); G01N 2333/775 (2013.01); G01N 2333/988 (2013.01)

(58) Field of Classification Search
CPC ............ C07K 7/08; A23L 33/18; A61K 38/00
See application file for complete search history.

(56) References Cited

U.S. PATENT DOCUMENTS 5,516,891 A 5/1996 Siwruk et al.
2005/0215499 A1* 9/2005 Guevara, Jr. ........ C07K 14/775
514/5.9
2011/0300172 A1* 12/2011 Nilsson ..................... A61P 9/10
435/69.3
2014/0308306 A1 10/2014 Chyu et al.
2017/0340702 A1* 11/2017 Carvlin .......... C12Y 406/01001

FOREIGN PATENT DOCUMENTS

JP 2010-208946 A 9/2010
KR 2017-0092829 A 8/2017
KR 2019-0085603 A 7/2019
WO 2014/204229 A3 12/2014
WO 2016/009436 A1 1/2016

OTHER PUBLICATIONS

International Search Report dated Oct. 31, 2019 in International Patent Application No. PCT/KR2019/008040, filed Jul. 2, 2019, 14 pages.
Stewart, J.M., "Solid Phase Peptide Synthesis", Pierce Chemical Company; Second Edition, Jan. 1, 1984, 176 pages.
Lee Joo Youn et al: "2794: Apolipoprotein B Binds to enolase-1 and aggravates Aggravates Inflammation in Rheumatoid Arthritis", Arthritis & Rheumatology; 2017 ACR/ARHP Annual Meeting, John Wiley & Songs, Inc, US, vol. 69, No. sUPPL. 10, Sep. 18, 2017 pp. 3984-3895,XP009525134.
European Search Report for EP1983149605 dated Feb. 25, 2022, all pages.
International Search Report and Written Opinion dated Oct. 31, 2019 in International Patent Application No. PCT/KR2019/008040, filed Jul. 2, 2019, 14 pages.
Ludwig, E.H., et al, "DNA sequence of the human apolipoprotein B gene", DNA vol. 6, Issue 4, Year 1987, GenBank: AAB00481.1, p. 363-372, DOI:10.1089/dna.1987.6.363. PMID: 3652907.
Lee, J.Y., et al. "Apolipoprotein B binds to enolase-1 and aggravates inflammation in rheumatoid arthritis." Annals of the Rheumatic Diseases, vol. 77, Issue 10, year 2018, 2 pages, doi:10.1136/annrheumdis-2018-213444.
Bae, S., et al, "α-Enolase expressed on the surfaces of monocytes and macrophages induces robust synovial inflammation in rheumatoid arthritis." Journal of Immunology, vol. 189, Issue 1 (Year 2012): 365-372. doi:10.4049/jimmunol.1102073.
Park, Y-B, et al. "Effects of antirheumatic therapy on serum lipid levels in patients with rheumatoid arthritis: a prospective study." The American Journal of Medicine, vol. 113, Issue 3, (Year 2002), p. 188-93. doi:10.1016/s0002-9343(02)01186-5.

(Continued)

Primary Examiner — Amber D Steele
(74) Attorney, Agent, or Firm — Kilpatrick Townsend & Stockton LLP

(57) ABSTRACT

A peptide for treating rheumatoid arthritis and use thereof are provided, and a peptide consisting of an amino acid sequence of SEQ ID NO: 1, SEQ ID NO: 3, or SEQ ID NO: 5 or a polynucleotide encoding the same, and a pharmaceutical composition for treating rheumatoid arthritis or a health functional food composition for improving rheumatoid arthritis, each including the peptide, are provided.

4 Claims, 12 Drawing Sheets

Specification includes a Sequence Listing.

(56) References Cited

OTHER PUBLICATIONS

Lee, J.Y., et al. "Apolipoprotein B binds to enolase-1 and aggravates inflammation in rheumatoid arthritis", Extended Report, Annals of the Rheumatic Diseases, vol. 77, Issue 10, year 2018, p. 1480-1489. doi:10.1136/annrheumdis-2018-213444.
Merrifield, R.B., et al, "Solid Phase Peptide Synthesis. I. The Synthesis of a Tetrapeptide", Journal of the American Chemical Society, vol. 85, Issue 14, Year 1963, 2149-2154, DOI: 10.1021/ja00897a025.

\* cited by examiner

PEPTIDE FOR TREATING RHEUMATOID ARTHRITIS AND USE THEREOF

TECHNICAL FIELD

The present disclosure relates to peptide for treating rheumatoid arthritis and use thereof.

BACKGROUND ART

Rheumatoid arthritis (RA) is a non-viral inflammatory disease, which chronically occurs in the synovial membrane of joints or tendons, and the synovial membrane may proliferate and the amount of synovia may increase accordingly, leading to swelling and pain of the joint. Rheumatoid arthritis affects many tissues and organs (skin, blood vessels, heart, lungs, or muscles) in the human body due to systemic inflammatory responses, and causes irreversible proliferative synovitis specifically to joints, which progresses to destruction of joint cartilage and stiffness of the joints. Although the cause of rheumatoid arthritis has not found yet, autoimmunity has been known to have a major role in chronic progress of this disease. More specifically, T cells have an important role in causing rheumatoid arthritis with the local release of inflammatory mediators or cytokines, and thus persistent autoimmune responses which lead to joint destruction occur. Major symptoms of rheumatoid arthritis are fatigue, feelings of helplessness, pain, etc., and the progress of rheumatoid arthritis is accompanied by fever and physical weakness. In addition, muscle spasticity and muscle atrophy occur around the inflamed joint, affecting joint movement.

Treatment of rheumatoid arthritis is primarily aimed at reducing joint pain and inflammation, preventing deformation of joints, and more fundamentally determining the intracellular functional mechanism causing rheumatoid arthritis and controlling the mechanism. Despite numerous studies on the causes and mechanisms of onset of rheumatoid arthritis and development of various new drugs based on the research results (Korean Patent Application No. 10-2018-003659), no drugs for a complete cure have yet to be developed.

Examples of known therapeutic agents of rheumatoid arthritis include nonsteroidal anti-inflammatory drugs (NSAIDs) (aspirin ibuprofen), methotrexate, leflunomide, sulfasalazine, steroid hormones, and so on. However, long-term intake of such therapeutic agents may cause side effects. Accordingly, in recent years, a soluble receptor of tumor necrosis factor (TNF) which plays a primary role in the inflammation mechanism, an antibody for TNF or interleukin 6 receptor, and an antibody for CD20, have been produced using gene recombinant techniques, and these substances have been developed as therapeutic agents, which considerably inhibit the progression of the disease. However, there is still a potential problem in that unexpected side effects such as severe infections, tuberculosis, or tumors may occur.

In view of these technical situations, there is a need to develop a new therapeutic agent which can alleviate various symptoms of rheumatoid arthritis, including inflammation or bone and cartilage erosion, by controlling the primary inflammation mechanism associated with rheumatoid arthritis.

DESCRIPTION OF EMBODIMENTS

Technical Problem

An aspect is to provide a peptide consisting of an amino acid sequence of SEQ ID NO: 1, SEQ ID NO: 3, or SEQ ID NO: 5, and a polynucleotide encoding the same.

Another aspect is to provide a pharmaceutical composition comprising the peptide or the polynucleotide encoding the same, as an effective ingredient, for preventing or treating rheumatoid arthritis.

Still another aspect is to provide a health functional food composition comprising the peptide as an effective ingredient, for preventing or treating rheumatoid arthritis.

Still another aspect is to provide a method screening a therapeutic agent of rheumatoid arthritis, comprising: (a) contacting apolipoprotein B100 (apoB100) with a subject sample comprising ENO1 (α-enolase) together with a candidate substance; and (b) comparing an apolipoprotein B100-ENO1 binding level, measured from the sample contacting with the candidate substance, with a control group without a candidate substance administered thereto.

Other objects and advantages of the present disclosure will be apparent by the appended claims and the following detailed description together with the attached drawings. The contents that are not set forth in the specification can be sufficiently recognized and inferred by a person skilled in the art to which the present disclosure belongs or the art similar thereto, and descriptions thereof will be omitted.

Solution to Problem

An aspect provides a peptide consisting of an amino acid sequence of SEQ ID NO: 1, SEQ ID NO: 3, or SEQ ID NO: 5, or a polynucleotide encoding the same, for treating rheumatoid arthritis.

As used herein, the term "peptide" means a polymer consisting of two or more amino acids connected by an amide bond (or a peptide bond), and more specifically the peptide may consist of an amino acid sequence of SEQ ID NO: 1, SEQ ID NO: 3, or SEQ ID NO: 5. The present inventors have made extensive efforts to develop a peptide having biologically effective activity, and as a result, they have elucidated a peptide consisting of an amino acid sequence of SEQ ID NO: 1, SEQ ID NO: 3, or SEQ ID NO: 5. The biologically effective activity may be a manifestation of one or more characteristics selected from (a) inhibition of the secretion of inflammatory cytokines; (b) alleviation of inflammatory responses due to rheumatoid arthritis; and (c) relaxation of pathological symptoms due to rheumatoid arthritis. Therefore, the peptide may be utilized for use in prevention or treatment of rheumatoid arthritis.

In addition, in order to obtain better chemical stability, reinforced pharmacological characteristics (half-life, absorptiveness, titer, efficacy, etc.), modified specificity (e.g., broad biological activity spectrums), and reduced antigenicity, the peptide may have a protecting group binding to the N- or C-terminal thereof. The protecting group is preferably an acetyl group, a fluoreonylmethoxycarbonyl group, a formyl group, a palmitoyl group, a myristyl group, a stearyl group and polyethylene glycol (PEG), but any component can be used without limitation so long as it is capable of modifying the peptide, specifically increasing the stability of the peptide. In a specific embodiment, the N-terminal of the peptide may bind to a protecting group selected from the group consisting of an acetyl group, a fluoreonylmethoxycarbonyl group, a formyl group, a palmitoyl group, a myristyl group, a stearyl group and polyethylene glycol (PEG), and/or the C-terminal of the peptide may bind to a protecting group selected from the group consisting of an amino group (—NH$_2$), and azide (—NHNH$_2$).

As used herein, the term "stability" refers to storage stability (e.g., room-temperature storage stability) as well as "in vivo" stability for protecting the peptide from the attack of in vivo protein cleavage enzymes.

In addition, the peptide may additionally comprise an amino acid sequence produced for a specific purpose for a target sequence, tag, or labeled residue.

As used herein, the term "polynucleotide" is a polymer having nucleotides linked, and refers to a molecule serving to transfer genetic information. The polynucleotide may encode the peptide consisting of an amino acid sequence of SEQ ID NO: 1, SEQ ID NO: 3, or SEQ ID NO: 5, and may include a sequence having a sequence homology of about 70% or higher, about 75% or higher, about 80% or higher, about 85% or higher, about 90% or higher, about 92% or higher, about 95% or higher, about 97% or higher, about 98% or higher, or about 99% or higher to that of the polynucleotide encoding the peptide.

As used herein, the term "homology" indicates sequence similarity to the amino acid sequence of a wild-type protein or the polynucleotide sequence. The homology may be compared using a comparison program that is widely known in the art, and homologies between two or more sequences can be computed and expressed as a percentage (%).

The peptide may be obtained in various methods widely known in the related art. In an example, the peptide may be produced using recombination of polynucleotides and a protein expression system, in vitro synthesis, such as peptide synthesis, and a cell-free protein synthesis method (solid-phase synthesis techniques; Merrifield, J. Amer. Chem. Soc. 85:2149-54(1963); Stewart, et al., Solid Phase Peptide Synthesis, 2nd. ed., Pierce Chem. Co.: Rockford, 111(1984), U.S. Pat. No. 5,516,891).

Another aspect provides a pharmaceutical composition comprising a peptide consisting of an amino acid sequence of SEQ ID NO: 1, SEQ ID NO: 3, or SEQ ID NO: 5 or a polynucleotide encoding the same as an effective ingredient, for preventing or treating rheumatoid arthritis.

In the pharmaceutical composition, the terms "peptide" and "polynucleotide" are the same as stated above.

As used herein, the term "prevention" may mean all actions in which the rheumatoid arthritis of a subject is restrained or retarded by the administration of the pharmaceutical composition according to an aspect.

As used herein, the term "treatment" may mean all actions in which the symptoms of rheumatoid arthritis are relieved or turned into better condition by the administration of the pharmaceutical composition according to an aspect.

As used herein, the term "subject" refers to a subject in need of treatment of rheumatoid arthritis and specifically refers to mammals, such as humans or non-human primates, mice, cats, horses, or cows.

According to an embodiment, the peptide may reduce secretion quantities of inflammatory cytokines, for example, IL-1β, IL-6, and/or TNF-α in blood, by inhibiting binding of apoB100 to ENO1 expressed on the surface of a mononuclear cell in peripheral blood, thereby demonstrating the efficacy in treating rheumatoid arthritis.

Meanwhile, the peptide according to an aspect and the polynucleotide encoding the same may be carried in a pharmaceutically acceptable carrier, such as a colloidal suspension, powders, a saline solution, lipids, liposomes, microspheres, or nano-spherical particles. The peptide or polypeptide may form a complex with a delivery vehicle or may be related thereto, and may be in vivo delivered using a delivery system known in the related art, such as lipids, liposomes, fine particles, gold, nanoparticles, a polymer, a condensation reactant, polysaccharide, polyaminoacid, dendrimer, saponin, an adsorption enhancing material, or fatty acid. The pharmaceutical composition may include a pharmaceutically acceptable carrier, which is commonly used in pharmaceutical formulations, including lactose, dextrose, sucrose, sorbitol, mannitol, starch, acacia, rubber, potassium phosphates alginate, gelatin, potassium silicate, microcrystalline cellulose, polyvinylpyrrolidone, cellulose, water, syrups, methylcellulose, methylhydroxy benzoate, propylhydroxy benzoate, talc, magnesium stearate, and mineral oils, and may further include a lubricant, a humectant, a sweetener, a flavoring agent, an emulsifier, a suspending agent, and a preservative, in addition to the ingredients stated above.

The pharmaceutical composition may be orally administered or may be administered parenterally (e.g., by intramuscular, intravenous, intraperitoneal, subcutaneous, intradermal, or local administration) according to the intended method, and a dosage amount of the pharmaceutical composition may vary depending on the patient's state, body weight, pathogenic state, drug type, administration route and administration time, and can be appropriately selected by a person skilled in the art.

The pharmaceutical composition is administered in a pharmaceutically effective amount. As used herein, the term "pharmaceutically effective amount" refers to an amount sufficient for treating a disease with a reasonable benefit/risk ratio applicable to medical treatment, and the level of effective dose may be determined based on factors including type of a patient's disease, severity, activity of drug, sensitivity for a used drug, administration time, administration route, an excretion rate, duration of treatment, drugs used simultaneously, and other factors well known in the medical field. The pharmaceutical composition according to an aspect may be administered as an individual therapeutic agent or in combination with another therapeutic agent, may be administered sequentially or simultaneously with a conventional therapeutic agent, and may be administered singly or multiply. It is important to administer the composition in the minimum amount that can exhibit the maximum effect without causing side effects, in view of all the above-described factors, and this amount can be easily determined by a person skilled in the art.

Specifically, the effect amount of the pharmaceutical composition may vary according to the patient's age, sex, state, body weight, absorption rate of bioactive ingredients, an inactivation rate, an excretion rate, type of disease, drugs co-administered with the pharmaceutical composition, and may be increased or decreased according to the administration route, severity of obesity, sex, body weight, or age.

Still another aspect provides a method for preventing or treating rheumatoid arthritis, comprising the step of administering to a subject a pharmaceutical composition comprising a peptide consisting of an amino acid sequence of SEQ ID NO: 1, SEQ ID NO: 3, or SEQ ID NO: 5 or a polynucleotide encoding the same as an effective ingredient.

The same terms or ingredients as those defined in the description of the pharmaceutical composition are the same as described above.

Still another aspect provides a health functional food composition comprising a peptide consisting of an amino acid sequence of SEQ ID NO: 1, SEQ ID NO: 3, or SEQ ID NO: 5 or a polynucleotide encoding the same as an effective ingredient, for preventing or treating rheumatoid arthritis.

In the health functional food composition, the term "peptide" is the same as described above.

As used herein, the term "improvement" may mean all actions that at least reduce a parameter related to the condition being treated, such as, for example, the degree of a symptom. Here, the health functional food composition may be used with a medication for preventing or improving rheumatoid arthritis simultaneously or separately, before or after the onset of the disease.

In the health functional food composition, the effective ingredients may be added as it is, or may be used with other food or food ingredients, and may be suitably used according to a conventional method. The amounts of the effective ingredients blended may be suitably determined according to the use purpose thereof (for prevention or improvement). Generally, the health functional food composition may be added in an amount of 15% by weight or less, preferably 10% by weight or less, based on the raw material in the preparation of food or beverages. However, in the case of long-term intake for the purpose of health and hygiene or for the purpose of controlling health, the amount may be less than the above range.

The health functional food composition may contain other ingredients without particular limitation in addition to the effective ingredients stated above. For example, the health functional food composition may contain various flavoring agents or natural carbohydrates as additional ingredients with conventional beverages. Examples of the natural carbohydrates may include a general sugar including: a monosaccharide, e.g., glucose, fructose, etc.; a disaccharide, e.g., maltose, sucrose; and a polysaccharide, e.g., dextrin, cyclodextrin, etc., and a sugar alcohol including xylitol, sorbitol, erythritol, etc. In addition to the flavoring agents, a natural flavor, e.g., thaumatin, *stevia* extract, etc., or a synthetic flavor, e.g., saccharin, or aspartame, etc. may be advantageously used. The ratio of the natural carbohydrates can be appropriately determined by a person skilled in the art.

In addition, the health functional food composition according to an aspect may contain various nutrients, vitamins, minerals (electrolytes), flavoring agents such as synthetic flavoring agents or natural flavoring agents, colorants, flavor enhancers (cheese, chocolate, etc.), pectic acid or its salt, alginic acid or its salt, organic acids, protective colloidal thickeners, pH adjusters, stabilizers, preservatives, glycerin, alcohol, carbonating agents used in carbonated drinks, etc. Such ingredients may be used independently or in a combination, and the ratio of the additive may be appropriately selected by a person skilled in the art.

Still another aspect provides a method for screening a therapeutic agent of rheumatoid arthritis, comprising: (a) contacting apolipoprotein B100 (apoB100) with a subject sample comprising ENO1 (α-enolase) together with a candidate substance; and (b) comparing an apolipoprotein B100-ENO1 binding level, measured from the sample contacting with the candidate substance, with a control group without a candidate substance administered thereto.

As used herein, the term "ENO1 (α-enolase)" is a multifunctional protein identified as a crucial element of a glycolytic pathway for the first time and is known to be ubiquitously expressed in a cellular matrix and expressed on the cell surface as a plasminogen-binding receptor. Antibodies for the ENO1 have been found in patient groups with autoimmune diseases including lupus, Crohn's disease, and retinopathy. However, little has been known about the binding of the ENO1 to a specific protein associated with induction of an inflammatory response of rheumatoid arthritis.

As used herein, the term "sample" may include whole blood, serum, plasma, saliva, urine, sputum, lymph fluid, cell, tissue, etc., isolated from a subject, and may be, for example, peripheral blood, and more specifically a peripheral blood mononuclear cell.

In the method, the term "contacting" is used in a general meaning, and may refer to binding two or more formulations (e.g., two polypeptides), or binding a formulation and a cell (e.g., a protein and a cell). The contacting may also occur in vitro. For example, the contacting may include binding of two or more formulations, binding of a test formulation and a cell, or binding of a cell lysate and a test formulation, in a test tube or another container. In addition, the contacting may also occur in cells or in situ. For example, a recombinant polynucleotide encoding two polypeptides may be coexpressed within cells, thereby contacting the two polypeptides in the cells or cell lysates. In addition, a protein to be tested may utilize protein chips arranged on the surface of a fixed bed or a protein array In the method, the "candidate substance" may include an arbitrary substance, a molecule, an element, a compound, an entity, or combinations thereof. For example, the candidate substance may include protein, polypeptide, small organic molecule, polysaccharide, polynucleotide, and so on. In addition, the candidate substance may be a natural product, a synthetic compound, a chemical compound, or a combination of two or more thereof.

The "method for measuring the binding level of apolipoprotein B100 and ENO1" may be one or more selected from the group consisting of two-hybrid assay, co-immunoprecipitation assay, co-localization assay, scintillation proximity assay (SPA), UV or chemical crosslinking assay, bimolecular interaction analysis (BIA), mass spectrometry (MS), nuclear magnetic resonance (NMR), fluorescence polarization assay (FPA) and in vitro pull-down assay.

According to an embodiment, a substance inhibiting binding of apolipoprotein B100 to ENO1 significantly reduced the secretion amount of inflammatory cytokine in the peripheral blood of a rheumatoid arthritis patient group and also showed excellent efficacy in treating rheumatoid arthritis animal models, and thus the binding level of apolipoprotein B100 to ENO1 can be utilized as an index in developing a therapeutic agent of rheumatoid arthritis.

Therefore, when the apolipoprotein B100-ENO1 binding level measured in the sample contacted with the substance material, compared with the control group, is decreased, the method may further include a step of determining the candidate substance as the therapeutic agent of rheumatoid arthritis. The change in the binding level may include a level similar to that of the control group or the positive control group, or reductions of 1%, 2%, 3%, 4%, 5%, 10%, 20%, 30%, 40%, 50%, 60%, 70%, 80%, 90%, and 100% or greater.

Advantageous Effects of Disclosure

According to an aspect, the peptide may significantly reduce the amount of inflammatory cytokine in the peripheral blood, and thus can be used in treating various symptoms of rheumatoid arthritis, such as inflammation, erosion of bone or cartilage tissues, etc.

In the screening method according to an aspect, a novel therapeutic agent capable of significantly reducing inflammatory responses associated with rheumatoid arthritis may be discovered.

MODE OF DISCLOSURE

Hereinafter, the present disclosure will now be described in greater detail with reference to the accompanying Examples below. However, these Examples are for illustrative purposes only, and should not be construed as being limited to the scope of the inventive concept in any way.

EXAMPLES

Example 1. Effect of ENO1-apoB100 Binding on Secretion of Inflammatory Cytokine

In this example, in order to identify the relation between rheumatoid arthritis and ENO1 expression on peripheral blood mononuclear cells, the ENO1 expression thereof was observed. In addition, it was attempted to identify the effect of binding ENO1 (α-enolase) to apolipoprotein B100 (apoB100) isolated from a rheumatoid arthritis patient and selected as an ENO1 (α-enolase) binding ligand on the secretion of inflammatory cytokine in the peripheral blood of the rheumatoid arthritis patient through proteomic analysis using immunoprecipitation (IP)/mass spectroscopy (MS). In detail, after ENO1 immunoblotting was performed on mononuclear cells obtained from the rheumatoid arthritis patient and peripheral blood mononuclear cells were treated with apoB100, changes in the secretion of IL-1β, IL-6 and TNF-α were compared. Meanwhile, a group in which cells isolated from healthy individuals are used (HC: healthy control) was determined as the control group.

Figure 1:
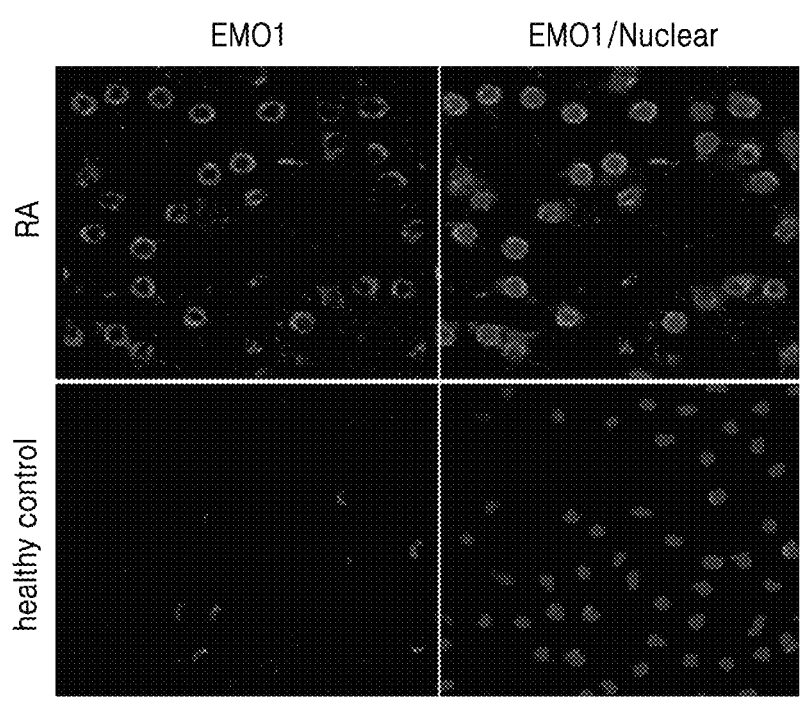
FIG. 1 shows the results of observation of ENO1 expressed on surfaces of peripheral blood mononuclear cells isolated from rheumatoid arthritis patients, as measured using a confocal microscope.
Figure 2:
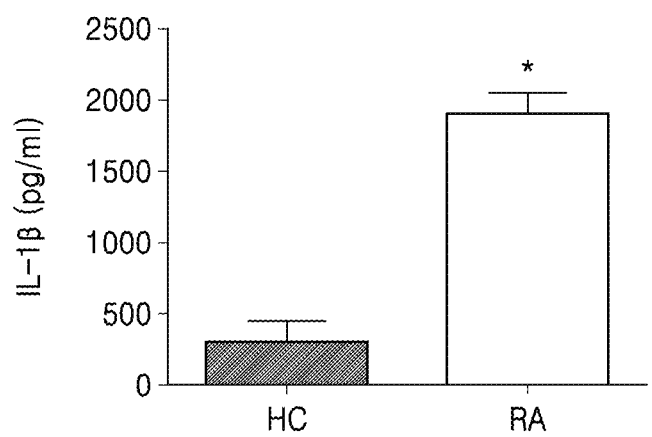
FIG. 2 shows the results of comparison of changes in the secretion of (A) IL-1β, (B) IL-6, and (C) TNF-α, after treating peripheral blood mononuclear cells isolated from rheumatoid arthritis patients with apoB100 (HC: healthy control group, RA: rheumatoid arthritis patient group, *p<0.05).
Figure 2:
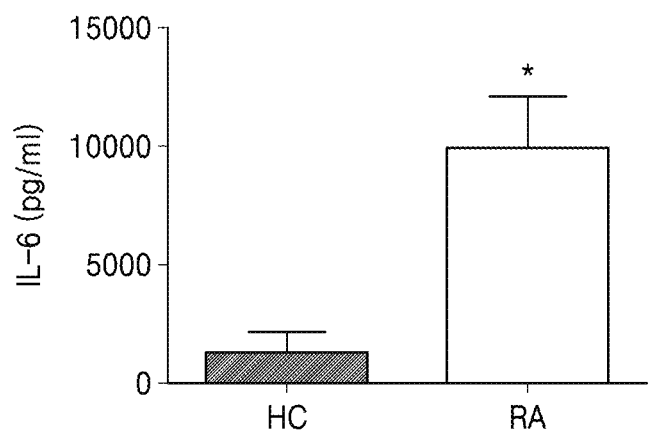
Figure 2:
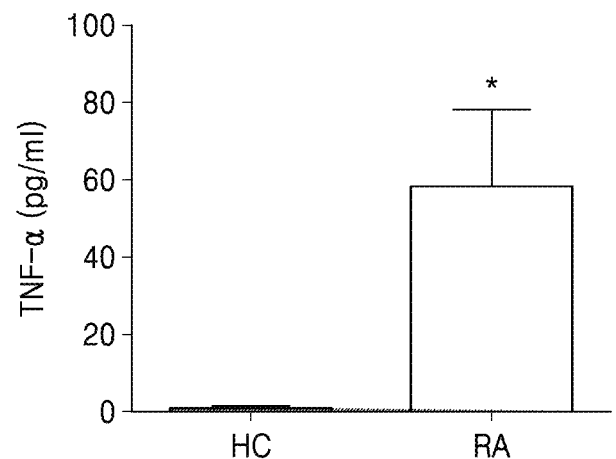

As shown in FIG. 1, the observation results showed that the ENO1 level expressed on the surface of the mononuclear cell isolated from the rheumatoid arthritis patient was significantly high, compared to the control group. In addition, the mononuclear cells isolated from the rheumatoid arthritis patients were treated with apoB100, and the results showed that the secretion levels of all of IL-1β, IL-6, and TNF-α as inflammatory cytokines were all markedly increased in the peripheral blood mononuclear cells, compared to the healthy control group, as shown in FIG. 2.

Figure 3:
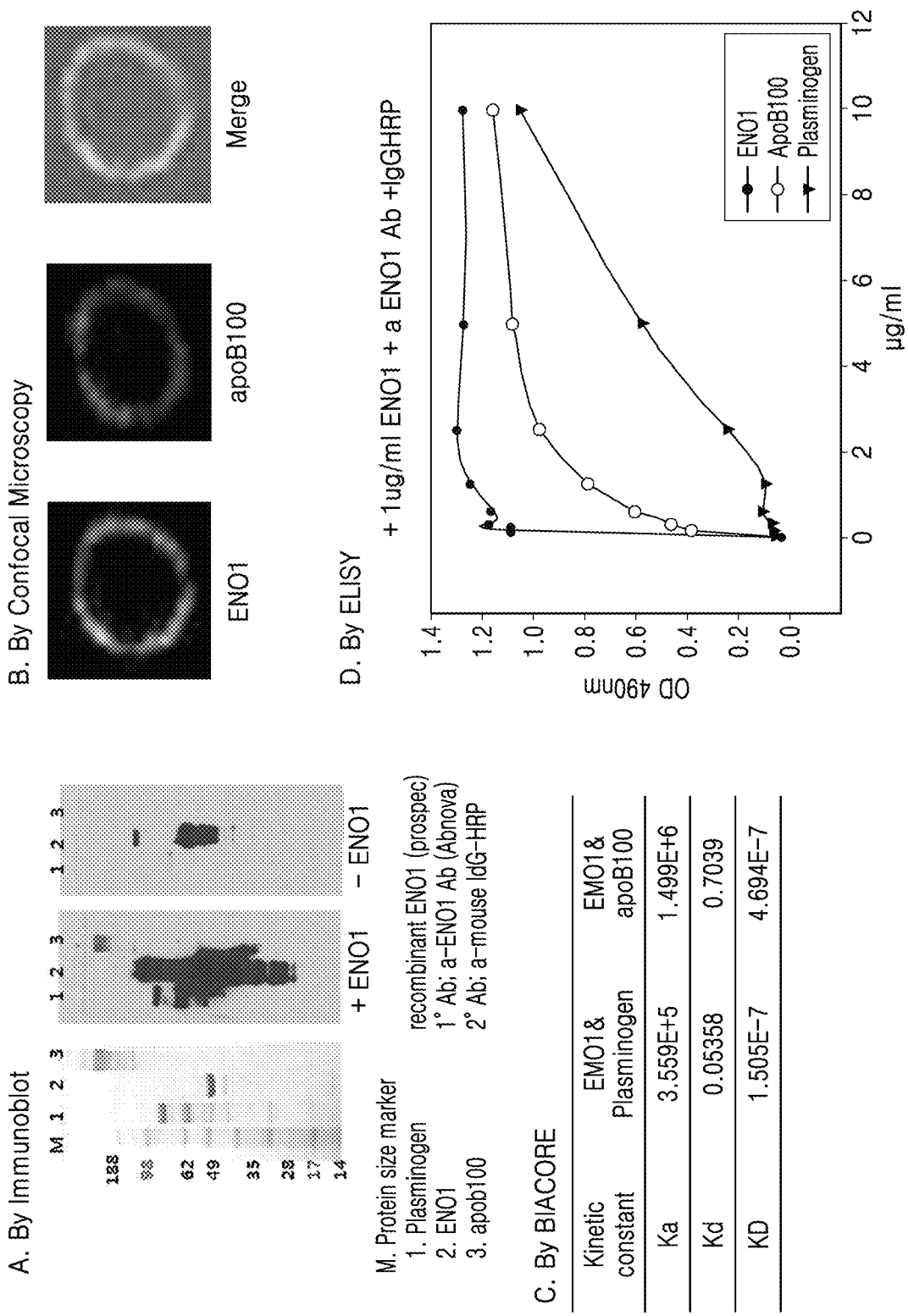
FIG. 3 shows the results of (A) immunoblotting, (B) confocal microscopy, (C) BIACORE system, and (D) ELISA assay, to identify apoB100-ENO1 binding.

In addition, ENO1-apoB100 binding was identified by immunoblotting, confocal microscopy, BIACORE system, and ELISA assay, and the results confirmed that, as shown in FIG. 3, ENO1 and apoB100 established relatively strong binding.

Accordingly, in this example, it was additionally verified whether the binding of ENO1 and apoB100 crucially affected inflammation responses due to rheumatoid arthritis. First, in a case where the ENO1 expression was inhibited by treating the peripheral blood mononuclear cell isolated from the rheumatoid arthritis patient with ENO1 siRNA, it was identified whether apoB100 treatment increased the secretion of inflammatory cytokines, like in the conventional case. In addition, since LDL existing in vivo in a state in which it binds to apoB100 protein may potentially involve the inflammation responses, LDLR knockout mouse and C57BL/6 wild-type mouse control group were treated with the serum of K/BxN mouse (referred to as K/BxN serum, hereinafter) and ApoB100, and resulting changes in vivo were compared. Meanwhile, addition of K/BxN mouse serum functions to induce rheumatoid arthritis through deposition of autoantibodies existing in the K/BxN serum, and is one of conventional techniques for manufacturing rheumatoid arthritis animal models by autoimmune responses.

Figure 4:
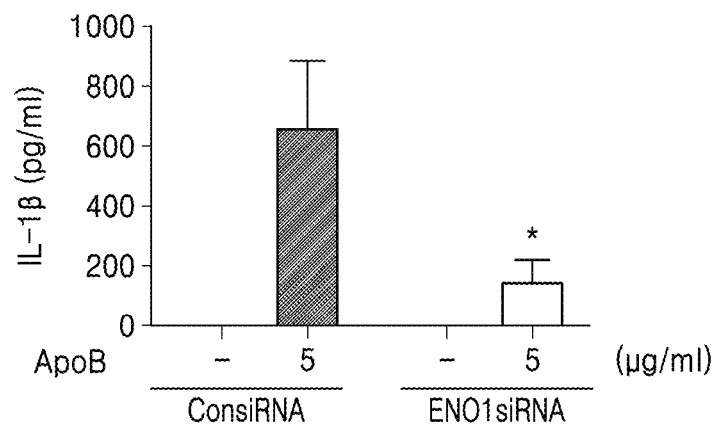
FIG. 4 shows the results of comparison of changes in the secretion of (A) IL-1β, (B) IL-6, and (C) TNF-α, after peripheral blood mononuclear cells isolated from rheumatoid arthritis patients were treated with ENO1siRNA to inhibit the expression of ENO1 and then treated with apoB100 (ConsiRNA: control group, ENO1siRNA: ENO1 expression inhibited group).
Figure 4:
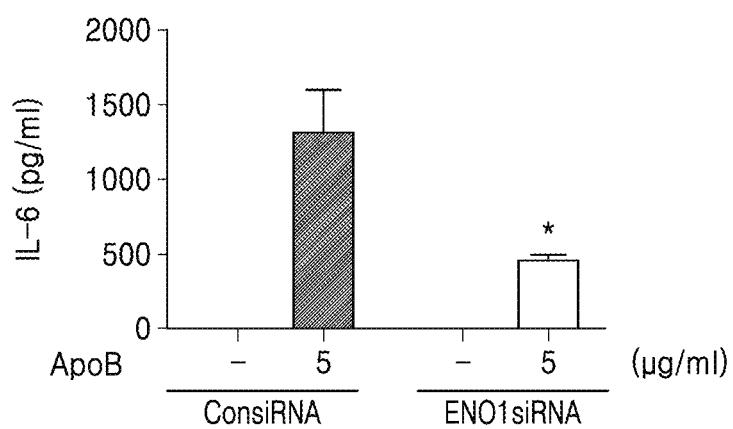
Figure 4:
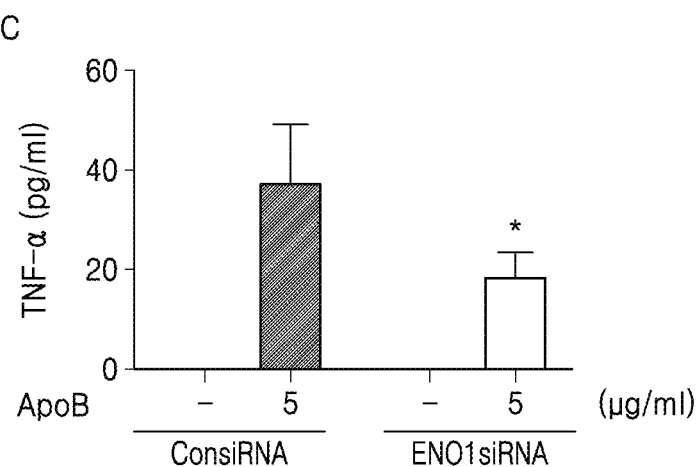
Figure 5:
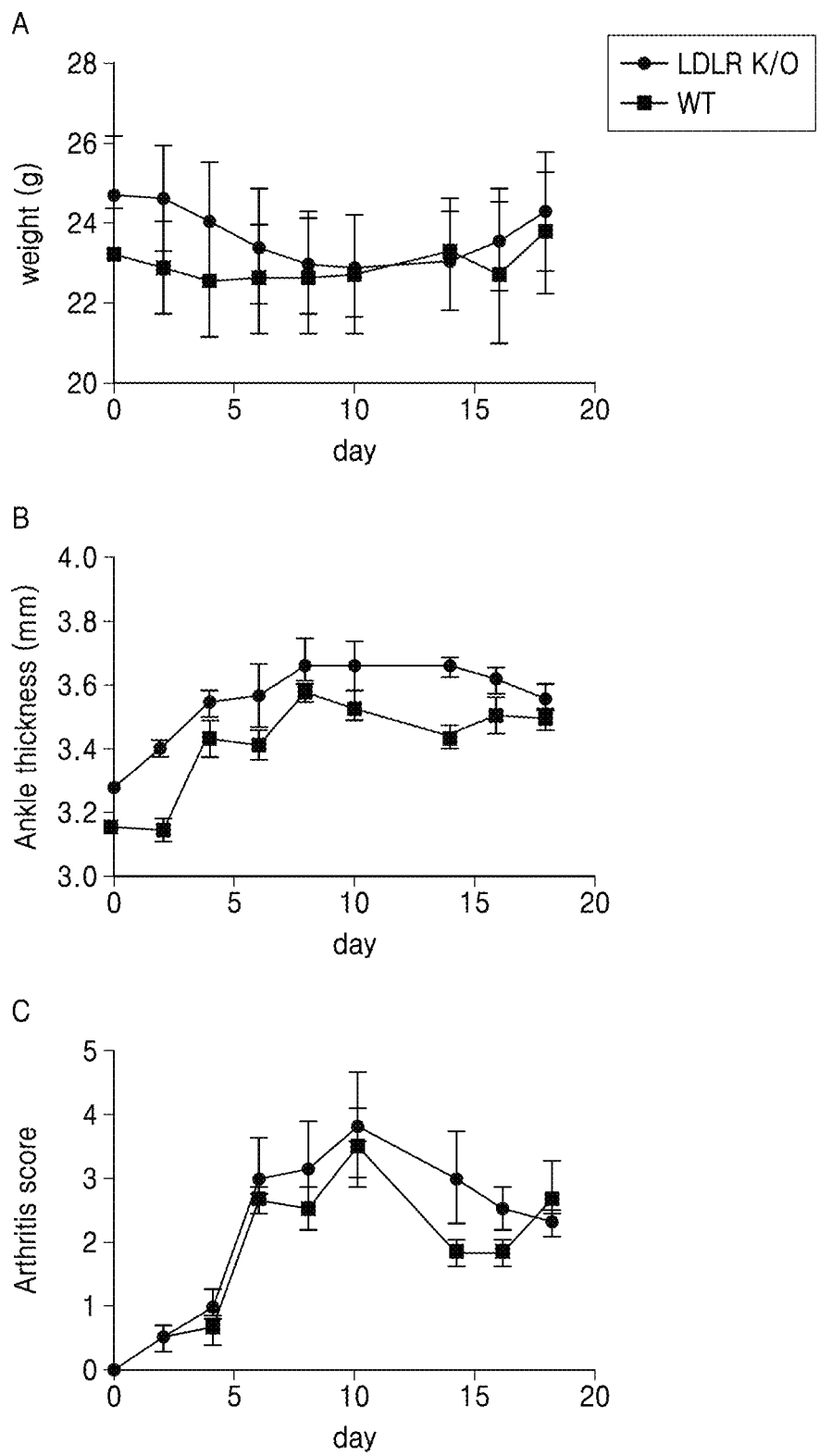
FIG. 5 shows the results of comparison of changes in (A) weight, (B) ankle thickness, and (C) arthritis score, after treating an LDLR knockout mouse and a wild-type mouse with apoB100 (LDLR K/O: LDLR knockout mouse, WT: wild-type mouse).
Figure 6:
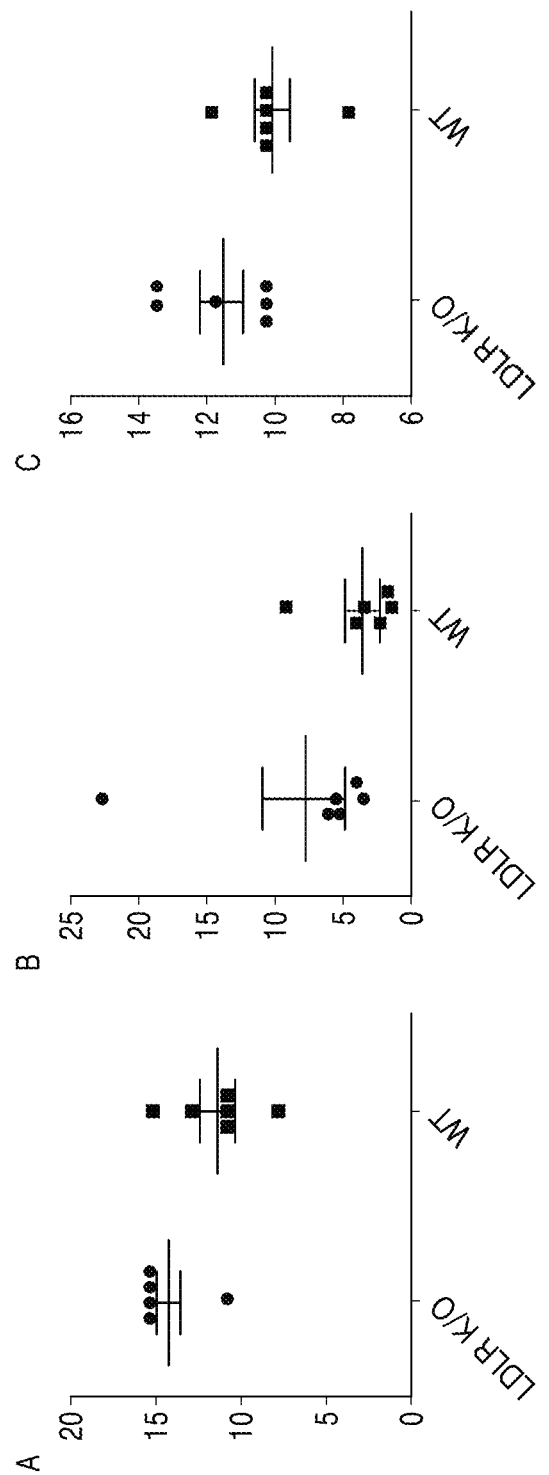
FIG. 6 shows the results of comparison of changes in the secretion of (A) IL-16, (B) IL-6, and (C) TNF-α, after treating LDLR knockout mouse and a wild-type mouse with apoB100 (LDLR K/O: LDLR knockout mouse, WT: wild-type mouse).

As a result, as shown in FIG. 4, when the ENO1 expression of peripheral blood mononuclear cells was inhibited, an increased secretion level of inflammatory cytokines was not observed by the apoB100 treatment. In addition, as shown in FIGS. 5 and 6, the results indicate that changes in the ankle thickness, arthritis score, and inflammatory cytokine secretion of the LDLR knockout mouse were similar to or higher than those of the control group, suggesting that the inflammation response is not relevant to LDL or LDL receptors.

That is, to sum up, the experimental results indicate that the onset of rheumatoid arthritis is closely related with the ENO1 expression of peripheral blood mononuclear cells, and it is particularly confirmed that the binding of ENO1 and apoB100 in peripheral blood plays a crucial role in the inflammation response of the relevant disease.

Figure 7:
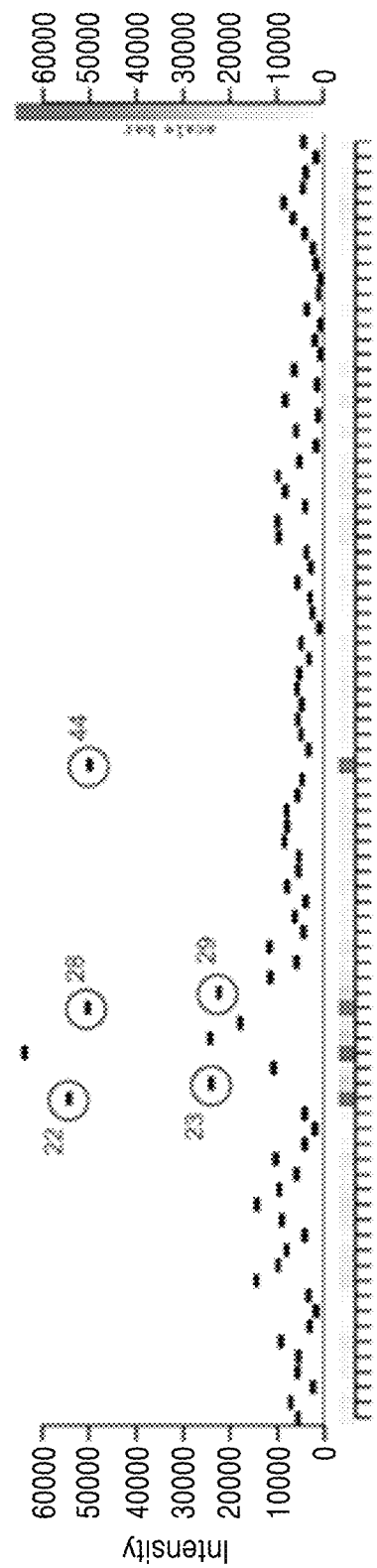
FIG. 7 shows apoB100 motifs binding to ENO1 in peripheral blood, as identified by peptide micro array.

Example 2. Deduction of Peptides for Inhibiting Secretion of Inflammatory Cytokine In this example, it was attempted to deduce peptides capable of inhibiting the secretion of inflammatory cytokine by inhibiting the binding of ENO1 in peripheral blood to apoB100, on the basis of the experimental results of Example 1. In detail, as shown in FIG. 7, apoB100 motifs binding to ENO1 were identified by peptide micro array, 5 peptides in total were obtained. Detailed information regarding the peptides is given in Table 1 below.

TABLE 1

| Number | Sequence information | Remarks |
|---|---|---|
| # 1 | AICKEQHLFLPF (SEQ ID NO: 1) | Represented with "22" in FIG. 7 |
| # 2 | CKEQHLFLPFSY (SEQ ID NO: 2) | Represented with "23" in FIG. 7 |
| # 3 | SYKNKYGMVAQV (SEQ ID NO: 3) | Represented with "28" in FIG. 7 |
| # 4 | KNKYGMVAQVTQ (SEQ ID NO: 4) | Represented with "29" in FIG. 7 |
| # 5 | TKKMGLAFESTK (SEQ ID NO: 5) | Represented with "44" in FIG. 7 |

Thereafter, peripheral blood mononuclear cells obtained from the healthy control and rheumatoid arthritis patients were treated with the peptides #1 to #5 (which are named apoB100 #1, apo100 #2, apoB100 #3, apoB100 #4, and apoB100 #5, respectively), and changes in the secretion of IL-1β, IL-6 and TNF-α were compared. Meanwhile, a non-binding peptide treated group (NBP) was determined as the control group, and the results of this example are indicated as the mean values of the secretion levels for each six of rheumatoid arthritis patients and healthy individuals.

Figure 8:
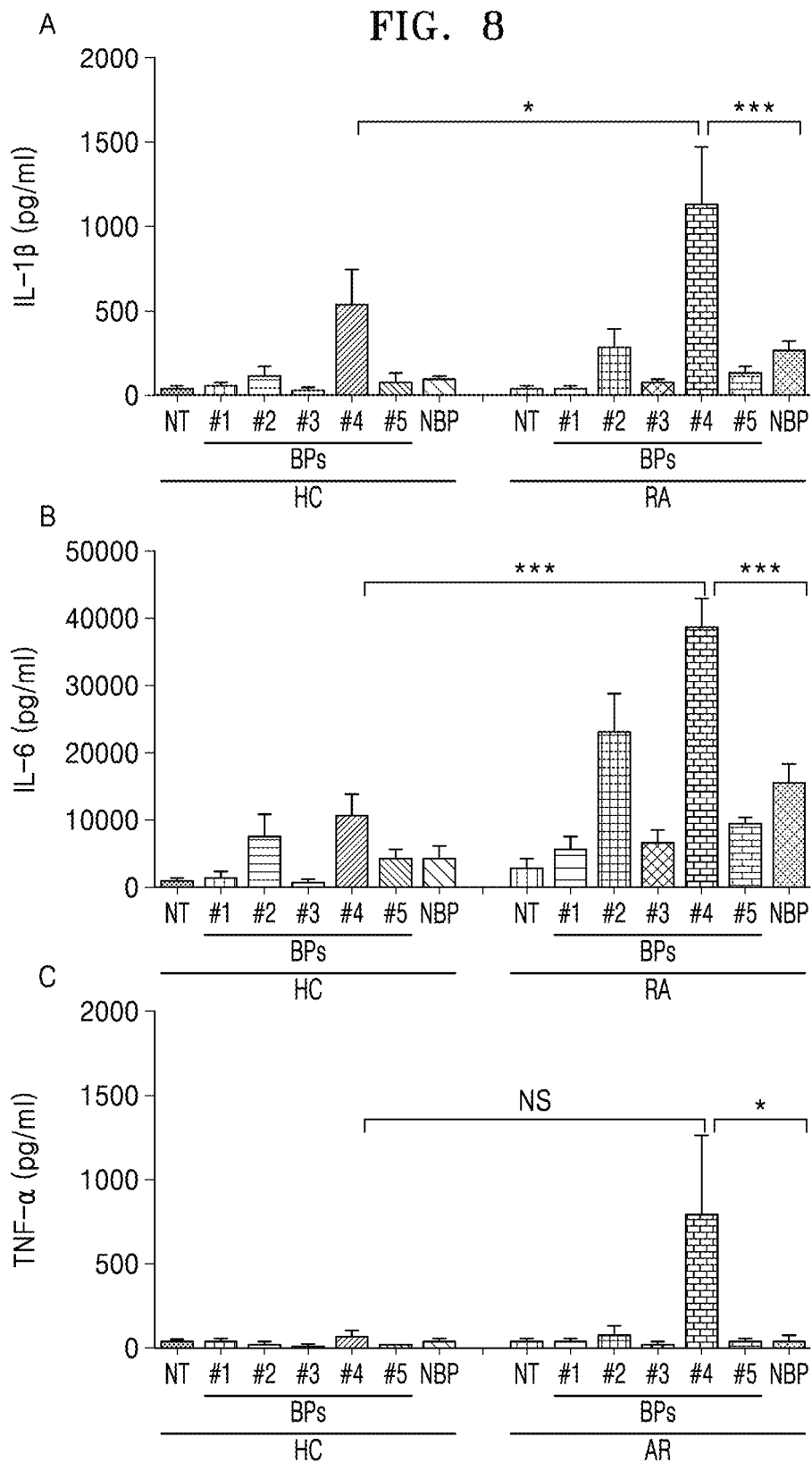
FIG. 8 shows the results of comparison of changes in the secretion of (A) IL-1β, (B) IL-6, and (C) TNF-α, after treating peripheral blood mononuclear cells isolated from rheumatoid arthritis patients with apoB100-derived peptides #1 to #5 (HC: healthy control group, RA: rheumatoid arthritis patient group, NBP: non-binding peptide treated group, *p<0.05, ***p<0.001).

As a result, as shown in FIG. 8, the secretion levels of IL-1β, IL-6 and TNF-α were significantly increased in the rheumatoid arthritis patients, compared to the healthy control (HC) group, which is the same as described above. In addition, when the mononuclear cells isolated from the rheumatoid arthritis patients were treated with apoB100 #2 or apoB100 #4, the results showed that the secretion levels of all of IL-1β, IL-6, and TNF-α were markedly increased in the peripheral blood mononuclear cells, compared to the healthy control group, while the secretion levels of IL-1β, IL-6, and TNF-α in the peripheral blood mononuclear cells treated with apoB100 #1, apoB100 #3 or apoB100 #5, the secretion levels of IL-1β, IL-6, and TNF-α were decreased.

Meanwhile, previous research has identified that the increased expression level of ENO1 in the blood of a rheumatoid arthritis patient was mostly derived from CD14 (+) peripheral blood mononuclear cells. Therefore, in this example, it was attempted to indirectly identify whether the binding of ENO1 to apoB100 involved the responses by comparing changes in the secretion levels of IL-1β, IL-6, and TNF-α, after treating the CD14(−) or CD14(+) peripheral blood mononuclear cells with the peptides #1 to #5. Meanwhile, a non-binding peptide treated group (NBP) was determined as the control group.

Figure 9:
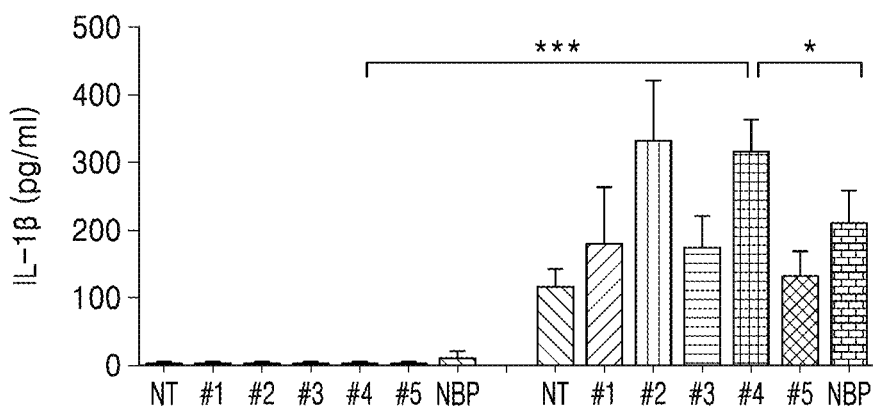
FIG. 9 shows the results of comparison of changes in the secretion of (A) IL-1β, (B) IL-6, and (C) TNF-α, after treating CD14(-) peripheral blood mononuclear cells and CD14(+) peripheral blood mononuclear cells with apoB100-derived peptides #1 to #5 (NBP: non-binding peptide treated group, *p<0.05, p<0.01, *p<0.001).
Figure 9:
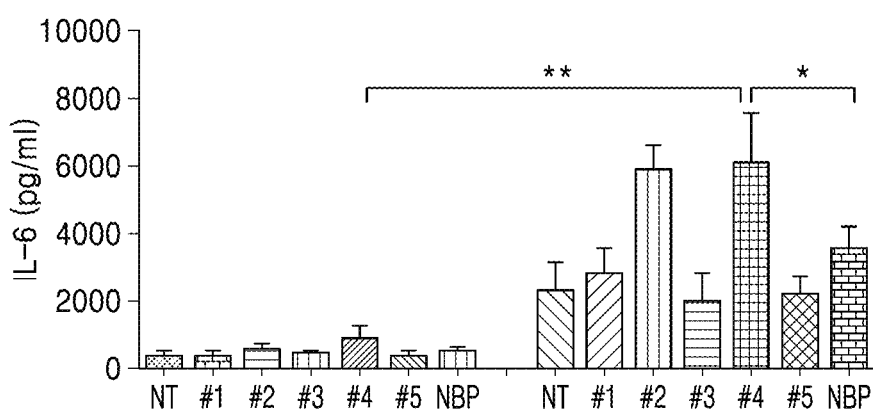
Figure 9:
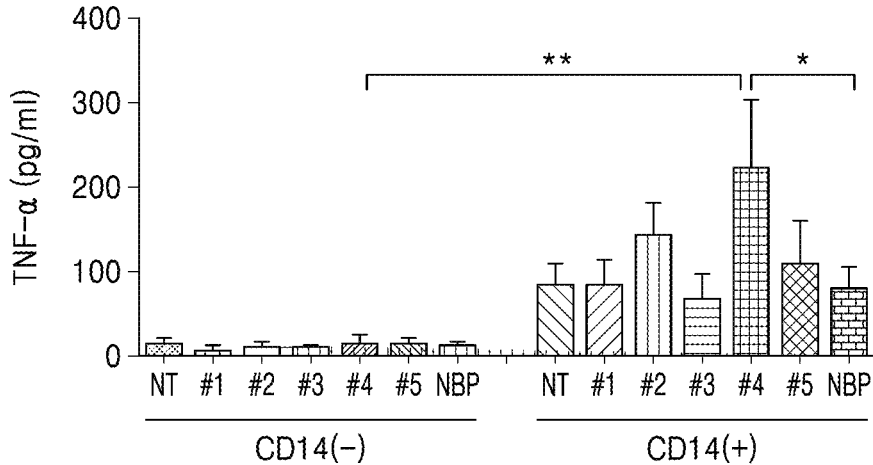

As a result, as shown in FIG. 9, the CD14(+) peripheral blood mononuclear cells showed a similar propensity to the result shown in FIG. 8, while no changes were observed in the CD14(−) peripheral blood mononuclear cells, further corroborating that the responses were closely related with the binding of ENO1 to apoB100.

On the basis of such experimental results, apoB100 #1, apoB100 #3, and apoB100 #5 were derived as peptides for inhibiting the secretion of inflammatory cytokine.

Example 3. Verification of Efficacy in Treating Rheumatoid Arthritis

In this example, it was attempted to verify the efficacy of the peptides (apoB100 #1, apoB100 #3, and apoB100 #5) for inhibiting the secretion of inflammatory cytokine, as in Example 2, in treating rheumatoid arthritis.

3-1. Decreased Secretion of Inflammatory Cytokine in Peripheral Blood Derived from Rheumatoid Arthritis Patient After peripheral blood cells derived from rheumatoid arthritis patients were treated with apoB100 #1, apoB100 #3, and apoB100 #5, changes in the secretion of IL-1β, IL-6 and TNF-α were identified. A non-binding peptide treated group (NBP) was determined as the control group.

Figure 10:
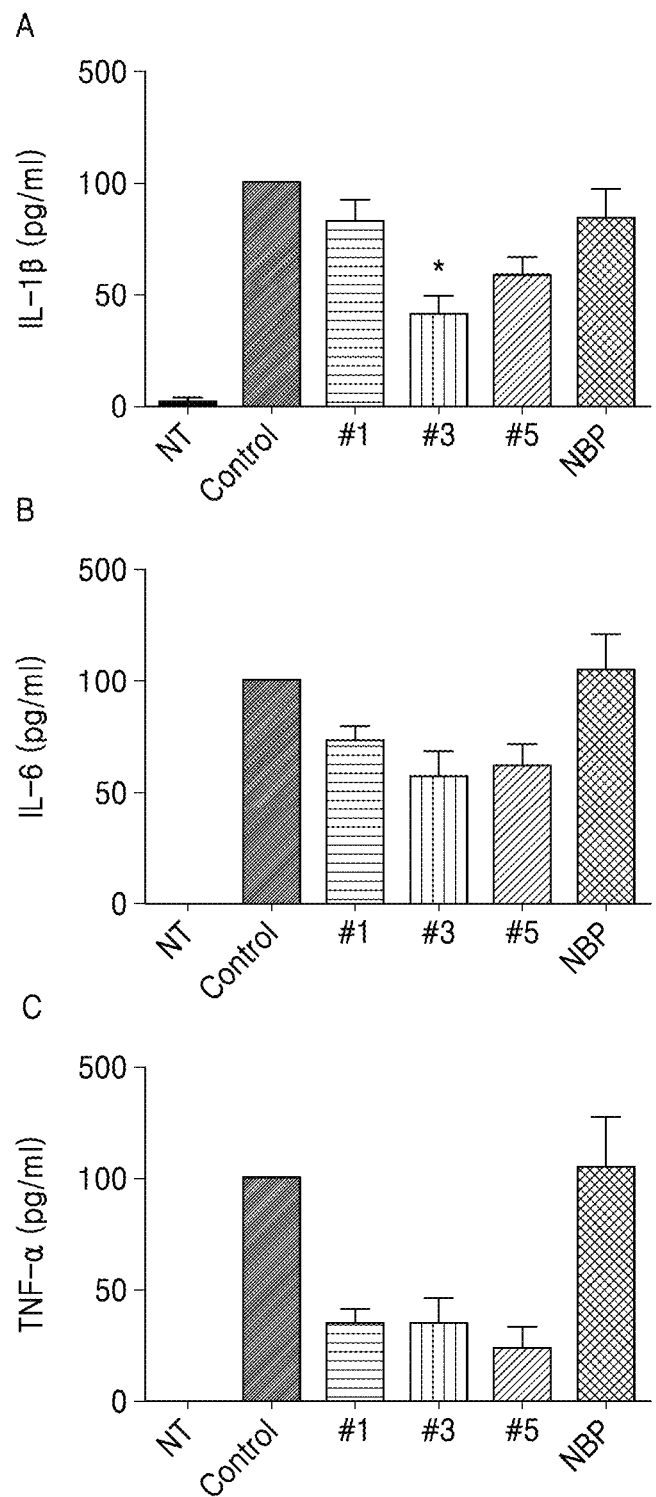
FIG. 10 shows the results of comparison of changes in the secretion of (A) IL-1β, (B) IL-6, and (C) TNF-α, after treating peripheral blood mononuclear cells isolated from rheumatoid arthritis patients with peptides for inhibiting the secretion of inflammatory cytokines (apoB100 #1, apoB100 #3, and apoB100 #5) (NBP: non-binding peptide treated group, *p<0.05).

As a result, as shown in FIG. 10, the secretion levels of IL-1β, IL-6 and TNF-α were significantly decreased with treatment with apoB100 #1, apoB100 #3 or apoB100 #5, and specifically, the treatment efficacy was highest when the treatment was made with apoB100 #3.

3-2. Identification of Efficacy in Treating Rheumatoid Arthritis Animal Models

K/B×N rheumatoid arthritis animal model (K/B×N serum transfer arthritis mouse) was established by inducing moderate rheumatoid arthritis by administering K/B×N serum and apoB to the mouse, and peptides for inhibiting the secretion of inflammatory cytokine were subcutaneously injected to the affected region of the animal model. Afterwards, changes in the ankle thickness and arthritis score resulting after peptide injection were identified. In addition, under the same conditions as described above, changes in the synovial inflammation, bone erosion, cartilage damage and leukocyte infiltration were compared. Meanwhile, groups treated with K/B×N serum and apoB only were determined as control groups, and groups treated with K/B×N serum and apoB, and a non-binding peptide treated group (NBP) were determined as comparison groups.

Figure 11:
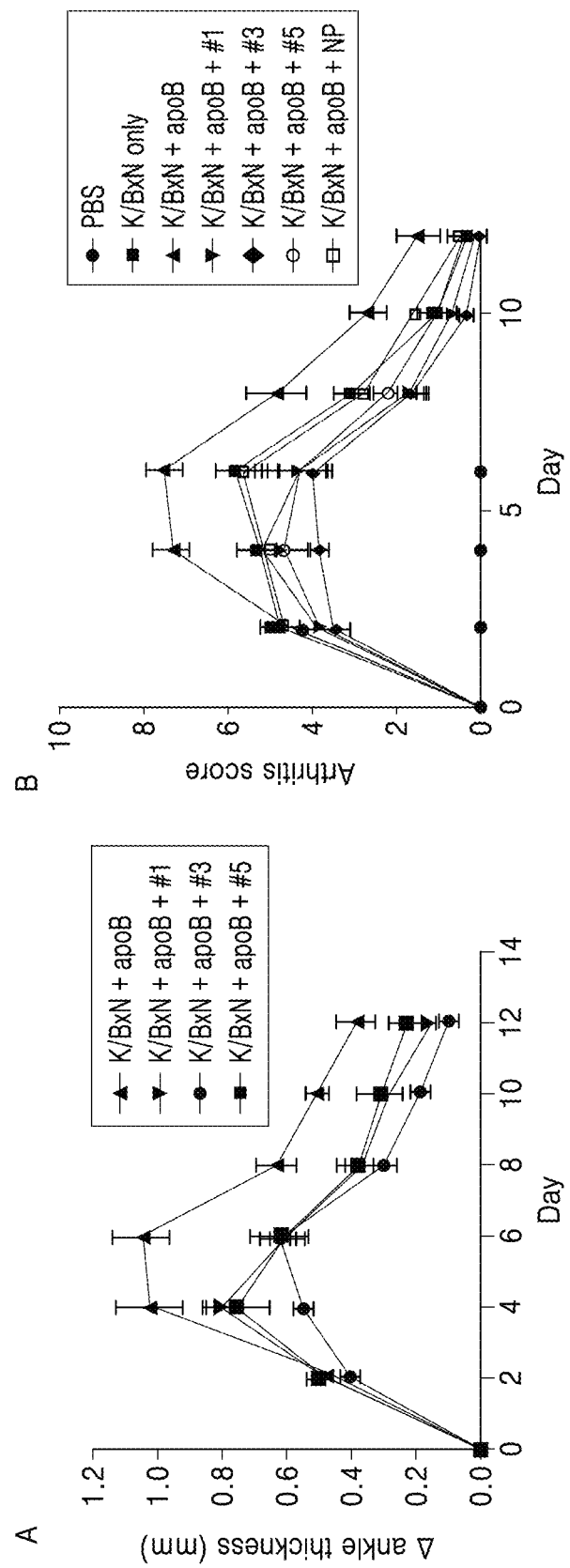
FIG. 11 shows the results of comparison of changes in (A) weight, (B) ankle thickness, and (C) arthritis score, after treating K/BxN rheumatoid arthritis animal models with peptides for inhibiting the secretion of inflammatory cytokines (apoB100 #1, apoB100 #3, and apoB100 #5).
Figure 12:
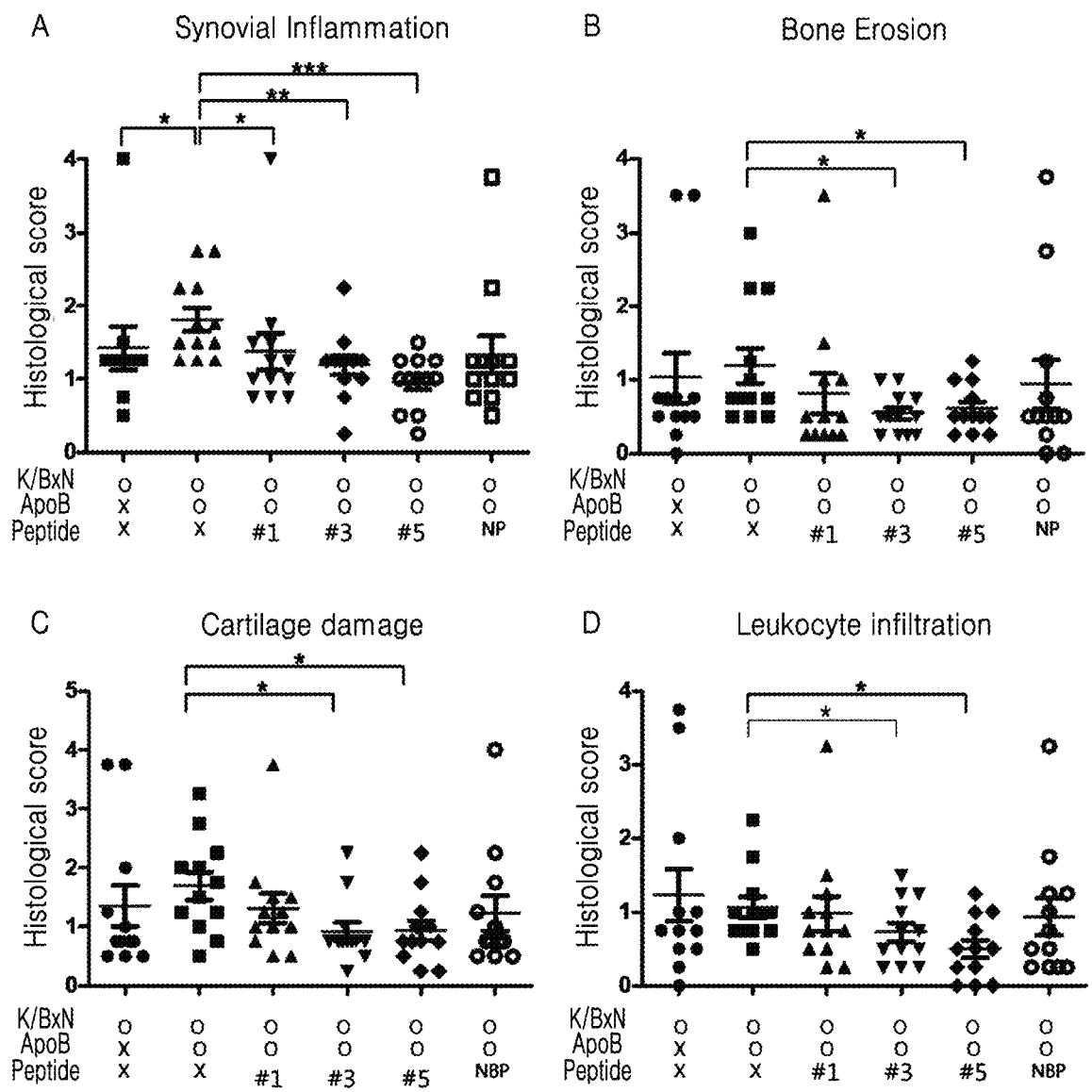
FIG. 12 shows the results of comparison of (A) synovial inflammation, (B) bone erosion, (C) cartilage damage, and (D) leukocyte infiltration, after treating K/BxN rheumatoid arthritis animal models with peptides for inhibiting the secretion of inflammatory cytokines (apoB100 #1, apoB100 #3, and apoB100 #5).

As a result, as shown in FIG. 11, the apoB100 #1, apoB100 #3 or apoB100 #5 treatment significantly decreased the ankle thickness and arthritis score increased due to rheumatoid arthritis. In addition, as shown in FIG. 12, similarly to the above results shown in FIG. 11, the synovial inflammation, bone erosion, cartilage damage and leukocyte infiltration were suppressed with treatment with the peptides. That is, to sum up, the experimental results indicate that the apoB100 #1, apoB100 #3, or apoB100 #5 can be used as the effective ingredient of a therapeutic agent for rheumatoid arthritis.

The foregoing description of the present disclosure has been provided for illustration, and it will be understood by those of ordinary skill in the art that various changes in form and details may be readily made therein without departing from the technical idea and essential features of the present disclosure. Therefore, it should be understood that embodiments described herein should be considered in a descriptive sense only and not for purposes of limitation.

The invention claimed is:

1. A method of treating rheumatoid arthritis, comprising administering to a subject in need thereof a pharmaceutical composition comprising a peptide consisting of the amino acid sequence of SYKNKYGMVAQV (SEQ ID NO: 3) wherein the N-terminus comprises an acetyl group and the C-terminus comprises an amino group.

2. The method of claim 1, wherein the pharmaceutical composition suppresses secretion of interleukin-1β (IL-1β).

3. The method of claim 1, further comprising concurrently, separately, or sequentially administering an additional anti-inflammatory agent.

4. The method of claim 1, wherein the pharmaceutical composition further comprises a pharmaceutically acceptable carrier.

* * * * *

SEQUENCE LISTING

```
<160> NUMBER OF SEQ ID NOS: 5

<210> SEQ ID NO 1
<211> LENGTH: 12
<212> TYPE: PRT
<213> ORGANISM: Artificial Sequence
<220> FEATURE:
<223> OTHER INFORMATION: peptide #1

<400> SEQUENCE: 1

Ala Ile Cys Lys Glu Gln His Leu Phe Leu Pro Phe
1               5                   10

<210> SEQ ID NO 2
<211> LENGTH: 12
<212> TYPE: PRT
<213> ORGANISM: Artificial Sequence
<220> FEATURE:
<223> OTHER INFORMATION: peptide #2

<400> SEQUENCE: 2

Cys Lys Glu Gln His Leu Phe Leu Pro Phe Ser Tyr
1               5                   10

<210> SEQ ID NO 3
<211> LENGTH: 12
<212> TYPE: PRT
<213> ORGANISM: Artificial Sequence
<220> FEATURE:
<223> OTHER INFORMATION: peptide #3

<400> SEQUENCE: 3

Ser Tyr Lys Asn Lys Tyr Gly Met Val Ala Gln Val
1               5                   10

<210> SEQ ID NO 4
<211> LENGTH: 12
<212> TYPE: PRT
<213> ORGANISM: Artificial Sequence
<220> FEATURE:
<223> OTHER INFORMATION: peptide #4

<400> SEQUENCE: 4

Lys Asn Lys Tyr Gly Met Val Ala Gln Val Thr Gln
1               5                   10

<210> SEQ ID NO 5
<211> LENGTH: 12
<212> TYPE: PRT
<213> ORGANISM: Artificial Sequence
<220> FEATURE:
<223> OTHER INFORMATION: peptide #5

<400> SEQUENCE: 5

Thr Lys Lys Met Gly Leu Ala Phe Glu Ser Thr Lys
1               5                   10
```